(12) United States Patent
Nakaoka et al.

(10) Patent No.: US 6,201,137 B1
(45) Date of Patent: Mar. 13, 2001

(54) PROCESS FOR PURIFYING TETRAHYDROFURANS USED AS STARTING MATERIAL FOR POLYETHER POLYOLS

(75) Inventors: Hiroshi Nakaoka; Toshiro Kubota, both of Yokohama (JP)

(73) Assignee: Hodogaya Chemical Co., Ltd., Kanagawa (JP)

(*) Notice: Subject to any disclaimer, the term of this patent is extended or adjusted under 35 U.S.C. 154(b) by 0 days.

(21) Appl. No.: 09/319,031

(22) PCT Filed: Sep. 29, 1998

(86) PCT No.: PCT/JP98/04369

§ 371 Date: Aug. 11, 1999

§ 102(e) Date: Aug. 11, 1999

(87) PCT Pub. No.: WO99/16762

PCT Pub. Date: Apr. 8, 1999

(30) Foreign Application Priority Data

Sep. 30, 1997 (JP) .................................................. 9-266450

(51) Int. Cl.$^7$ ........................ C07D 307/06; C07D 307/08
(52) U.S. Cl. ........................ 549/429; 549/509; 528/417

(58) Field of Search ................................ 549/429, 509; 203/34, 35

(56) References Cited

U.S. PATENT DOCUMENTS

| 3,450,608 | * | 6/1969 | Craig ....................................... 204/59 |
| 3,969,344 | | 7/1976 | Ackermann et al. ................. 549/429 |
| 5,319,111 | * | 6/1994 | Zimmermann et al. ............. 549/508 |

FOREIGN PATENT DOCUMENTS

| 47-10466 | 5/1972 | (JP) . |
| 61-200979 | 9/1986 | (JP) . |

* cited by examiner

*Primary Examiner*—Bernard Dentz
(74) *Attorney, Agent, or Firm*—Pillsbury Madison & Sutro LLP

(57) ABSTRACT

Tetrahydrofurans suitable for use as starting materials in the synthesis of polyether polyols without causing coloration in the product polyether polyols can be obtained by contacting crude tetrahydrofurans with a mineral acid or a strongly acidic cation-exchange resin, followed by isolation through a simple distillation and/or rectification to obtain purified tetrahydrofurans.

11 Claims, No Drawings

PROCESS FOR PURIFYING TETRAHYDROFURANS USED AS STARTING MATERIAL FOR POLYETHER POLYOLS

This application is the national phase on international application PCT/JP98/04369 filed Sep. 29, 1998 which designated the U.S.

BACKGROUND OF THE INVENTION

1. Field of the Invention

The present invention relates to a method for purifying crude tetrahydrofurans such as tetrahydrofuran or alkyl tetrahydrofurans. The purified tetrahydrofurans (hereinafter shortened to THF) obtained by this invention are suitable to use as starting materials in the preparation of a polyether polyols. Such polyether polyols are very important because these materials are used in the preparation of polyurethane or polyester for use in elastomers or spantex. Polyurethane resins obtained by the co-polymerization of alkyl THF and THF exhibit superior elastic properties, resistance to lower temperature and hydrolysis, and consequently, are industrially useful substances in the chemical industry.

2. Description of the Prior Art

Many methods have been proposed for the purification of THF. For example, through the use of bleaching earth, Japanese Patent Publication 61-54029 obtained THF having a low carbonyl, bromine and peroxide content. There is, however, neither a stated objective of purifying nor disclosure directed to any kind of impurity. The removal of another THF impurity, THF peroxide, has been described in Japanese Patent Laid Open Publication 54-88256, by treatment with an activated carbon layer.

Further, aromatic aldehydes are an impurity in crude THF. A method to obtain THF from which aldehydes, such as n-buthylaldehyde, are removed is disclosed in Japanese Patent Publication 52-29. It involves a distillation following treatment with a primary amine having a high boiling point and non-volatile acid. These latter disclosed methods may be characterized as targeting a specified impurity, however, the procedure by which THF before purifying is prepared and the usage of the purified THF are not disclosed. Still further, when a primary amine of a high boiling point and non volatile acid are used alone, obtaining a purified THF would not be expected. Indeed, as disclosed in the aforesaid Japanese patent publication, they must be used together in order.

Aldehydes are also an impurity in THF that must be removed. For example, a method to obtain THF having less than 50 ppm aldehyde impurity is disclosed in Japanese Patent Laid open publication 54-88256. It involves treatment with boron hydride and afterwards distillation. In this publication, it is disclosed that when poly-oxitetramethyleneglycol (hereinafter shortened to PTMG) is prepared using THF which contains aldehydes, PTMG becomes colored.

A reported purification method directed towards THF obtained by the Reppe method comprises a distillation, a contact hydration in the presence of Raney nickel and a subsequent distillation is described in Japanese Patent Laid open publication 57-28076. In this publication, substances are listed which cause discoloration of the glycol polymer produced from THF, however, the substance mainly responsible for discoloration is not disclosed. In addition, expensive materials must be used when purifying THF by this method.

THF purified by the method disclosed in Japanese Patent Publication 10-29280 is obtained in greater than 99.9% purity. However, the disclosed process is lengthy and uses expenses materials. Crude THF is contacted with water and/or acetic acid in the presence of a high acid cationic ion exchanging resin. The acetic is then removed by distillation. The THF is then hydrated in the presence of a precious metal catalyst, and then purified by further distillation. In this method, the impurities to be removed are limited to dihydrofuran and N-butylaldehyde, and it is reported that PTMG obtained from this high purity THF is not colored. However, this reference provides no clarification as to which compound is responsible for the discoloration.

SUMMARY OF THE INVENTION

Methods for purifying THF which prevents the coloring of PTMG obtained by a ring-opening polymerization have been reported in many papers, as mentioned above. However, in the case of producing high purity THF, which must reliably prevent coloring, long and expensive procedures must be used. In contrast, tetrahydrofurans used for the preparation of polyether polyols need only be sufficiently pure to prevent the polyether polyol from coloring, and need not necessarily be of high purity.

To discover an economic and facile method for purifying crude THF, the inventors investigated the mechanism of coloring of polyether polyol to identify which impurity among the many impurities must be removed in order to prevent the polyether polyol from being discolored. In addition, it was also necessary to clarify the cause of coloring of alkyl THF and to establish a method for purifying alkyl THF. The impurities contained in alkyl THF more seriously affect the coloring problem of obtained polyether polyol than the impurities contained in THF.

Further, when PTMG obtained by a ring-opening polymerization and polyether polyol obtained by a copolymerization of alkyl THF and THF are compared, the latter is more easily handled because it has a lower melting point and is liquid at the room temperature. These compounds also form desirable polyurethanes because of their physical properties in the low temperature region. Consequently, advantageous elastic recovery ratios, as well as greater strength and elongation, are present in polyurethanes obtained alkyl THF copolymers.

After extensive studies it has been found that the impurities responsible for polyether polyol coloration of alkyl THF and the coloring of THF are vary similar. After investing the coloring mechanism of polyether polyol it was found that dihydrofuran is the impurity which mainly causes the coloring problem. It was further found that mineral acid can satisfactorily remove these undesirable dihydrofuran compounds, and thus accomplished the present invention.

An object of the present invention is to provide a sufficient method for purifying THF to obtain compounds suitable for use as starting materials in the synthesis of polyether polyols. Another object of the present invention is to provide a method for purifying THF compounds to remove the impurity causing the discoloration of polyether polyol, regardless the preparation method of crude THF.

These and other objects are achieved by the present method for purifying tetrahydrofurans suitable for use in the synthesis of polyether polyols. This method comprises contacting crude tetrahydrofurans represented by general formula (1)

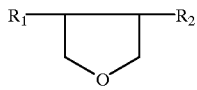

wherein, $R_1$ and $R_2$ represent, independently, a hydrogen atom or an alkyl group of 1 to 5 carbon atoms, with mineral acid or a high acid cationic exchanging resin, separating the acidic material from the THF, followed by recovery of the THF by simple distillation and/or rectification to obtain the purified THF.

In another embodiment, crude tetrahydrofurans may be purified by contacting said tetrahydrofurans with a mineral acid which is then neutralized by adding an aqueous alkaline solution containing more than one equivalent by volume, relative to mineral acid, of an alkali metal salt or an alkaline-earth metal salt, followed by simple distillation and/or a rectification.

In the present invention, the entire process for purifying THF can be carried out in series, in whole or part.

Further, the present invention also concerns the tetrahydrofurans suitable for use in the synthesis of polyether polyols, which tetrahydrofurans are purified by a simple distillation and/or a rectification after the crude tetrahydrofurans represented by general formula (1) are contacted with a mineral acid or a high acid cationic ion exchanging resin and separated therefrom. In general formula (1),

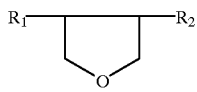

$R_1$ and $R_2$ independently represent a hydrogen atom or an alkyl group having from 1 to 5 carbon atoms.

Furthermore, the purified tetrahydrofurans produced by this invention, which may be used as starting material in the synthesis of polyether polyols, can also be prepared by a method comprising contacting crude tetrahydrofurans with a solution of 0.1 to 15 percent by weight mineral acid followed by a simple distillation and/or a rectification. Still more preferably the acid solution used contains between 2 and 10 weight percent mineral acid.

Still further, tetrahydrofurans used as starting materials for polyether polyols of this invention, may also be prepared by a purification method comprising contacting crude tetrahydrofurans with a mineral acid, then adding an alkaline aqueous solution containing a quantity of alkali metal salt or alkaline-rare earth metal salt that is greater than the equivalent quantity to the quantity of used mineral acid used, followed by a simple distillation and/or a rectification.

By the purifying method of this invention, the substance which causes the coloring problem in the preparation of polyther polyol can be specifically removed. The substance mainly responsible for the coloring problem in the preparation of polyether polyol are dihydrofurans. In a case of THF, the dihydrofurans include 2, 3-dihydrofuran, 2,5-dihydrofuran, hydroxy THF (hydrolysis product of dihydrofuran), γ-hydroxybuthylaldehyde (isomer of hydroxy THF) and the condensation product of γ-hydroxybuthylaldehyde. In a case of an alkyl THF, alkyl substituted dihydrofurans of the above mentioned dihydrofurans can also cause discoloration. Commonly, dihydrofurans are contained as impurities in crude THF, irrespective of the method by which the crude THF is prepared.

Unsaturated aldehydes are secondary agents responsible for discloloration. Other aldehydes can also contribute to the coloring problem, but to a lesser degree.

Among the dihydrofurans, dihydrofuran is especially hard to remove, because the boiling point of this compound is very close to that of THF. It is assumed that dihydrofuran is converted, by reaction with the mineral acid of the present invention, to hydroxy THF, γ-hydroxybuthylaldehyde, or the condensed substance γ-hydroxybuthylaldehyde. In a case of alkyl dihydrofuran, it is also assumed that a like conversion occurs following treatment with mineral acid as is the case with dihydrofuran. The substances which cause the coloring problem, such as unsaturated aldehydes and other aldehydes, can be converted to a condensation product by mineral acid, that can be easily removed from THF by subsequent distillation.

The procedure to purify crude THF is simplified by the method of the present invention, and the operation is very easy. The solution/mixture obtained after the tetrahydrofurans have been contacted with mineral acid, may be immediately distillated by a simple distillation or a rectification. In the case of neutralization by adding an alkaline aqueous solution after crude tetrahydrofurans are contacted with mineral acid, it is possible to immediately proceed with a simple distillation or a recitification after the neutralization. If the crude tetrahydrofurans are contacted with a high acid cationic ion exchanging resin, it is also possible to immediately proceed with a simple distillation or a rectification.

This method is useful for purifying tetrahydrofurans for use in polyether polyol synthesis because it is possible to satisfactorily remove the substance causing coloring (discoloring) of the polyether polyol when prepared from THF.

DETAILED DESCRIPTION OF THE INVENTION

THF which may be purified by the method of this invention can be prepared by the Reppe method, the phthalic acid anhydride method, the butadiene method or the furfural method. Further, the secondary product from the polyester manufacturing process which uses 1,4-buthanediol and purified THF of PTMG manufacturing process.

THF compounds represented by general formula (1), include, for example the following:
tetrahydrofuran,
3-methyl tetrahydrofuran,
3-ethyl tetrahydrofuran,
3-propyl tetrahydrofuran,
3-buthyl tetrahydrofuran,
3-pentyl tetrahydrofuran,
3,4-dimethyl tetrahydrofuran,
3,4-diethyl tetrahydrofuran,
3,4-dipropyl tetrahydrofuran,
3,4-dibuthyl tetrahydrofuran,
3,4-dipentyl tetrahydrofuran,
3-methyl-4-ethyl tetrahydrofuran; and
3-methyl-4-propyl tetrahydrofuran.

Minerals acids such as, nitric acid, sulfuric acid and phosphoric acid can be used. The concentration of the mineral acid is not restricted. However, if it is too dilute, the quantity of water to be added must be decreased. Thus, solutions from 0.1 to 15 weight percent, more preferably between 1 to 10 weight percent of mineral acid are added to crude THF.

Suitable high acid cationic ion exchange resins include aromatic sulfonic acid type cationic ion exchanging resins or benzyl sulfonic acid type cationic ion exchange resins. As the base resin for the above mentioned further exchange resins, styrene type, acrylic type, methacrylic type and phenolic-type resins can be used. Both the batch method and tower method can be used as a treating method when using high acid cationic ion exchanging resin. The quantity to be used is from 1 to 30 weight percent relative to THF.

The contact temperature range is from room temperature to over the boiling point of THF. If it is necessary to carry out the simple distillation or the rectification immediately after the contact process, the purifying process can be effectively simplified by setting the temperature of mineral acid higher than the boiling point of THF.

The above mentioned processes can be operated by series.

A method of purifying THF according to the invention can be carried out as follows. First 0.1 to 15 wt. %, preferably 1 to 10 wt. % of mineral acid is added to the crude THF. The contents are stirred for 1 to 10 hours, preferably 1 to 3 hours, at a temperature ranging from room temperature to the boiling point of THF, more preferably from 40° C. to 50° C., and then cooled. After cooling, the contents are neutralized by adding an alkaline aqueous solution of 1 to 50 wt. %, preferably 40 to 50 wt. %, containing the same or greater gram equivalent, preferably 1 to 1.2 gram equivalents, of alkali metal salt, and then purified by a simple distillation or a rectification.

The simple distillation or rectification can be also carried out without neutralization by alkaline solution. In the case of high acid cationic ion exchanging resin, 1 to 30 wt. %, preferably 5 to 10 wt. %, of a highly acidic cationic ion exchange resin is added to the crude THF, the contents are stirred for 1 to 10 hours, preferably for 1 to 3 hours, at a temperature ranging from the room temperature to the boiling point of THF, more preferably from 40° C. to the boiling point of THF, and then filtered. The THF recovered via filtration is dehydrated and purified by rectification. It is not necessary to reclaim the high acid cationic ion exchanging resin and this process is possible until the base resin is deteriorated.

Further, the continuous method is more effective. According to this embodiment, the highly acidic cationic ion exchange resin is packed into a column. The temperature of the column is kept at 40° C. to 80° C., preferably 40° C. to 50° C. The crude THF is then continuously introduced, e.g., poured, into the top of the column. The THF flowing out from the bottom of the column is then distilled.

EXAMPLES

Synthetic method of PTMG

To a 500 ml flask was added 200 g of THF and 8.8 g of 70 wt. % $HClO_4$ aqueous solution. The solution was cooled to 5° C., titrated with 48.0 g of acetic anhydride over 30 minutes, and then stirred for 8 hours, while maintaining the temperature at 5° C. The reaction is then quenched with 190.5 g of 17 wt. % aqueous solution of sodium hydroxide with stirring, the flask is settled and the water layer is removed. 47.1 g of 30 wt. % aqueous solution of sodium hydroxide is added to the oil layer, which is then heated to 120° C. so as to distill off the unreacted monomer, then 140 g of n-butanol, reflux for 3 hours and saponificate the contents. After settling, the water layer is removed, and 94.0 g of water is added to the oil layer. The contents are refluxed with constant stirring for 15 minutes. The contents in the flask are allowed to settle and cooling. The water layer is removed and the oil layer is rinsed with a water. Further, the oil layer is repeatedly rinsed 3 times by water adjusted to pH 2 to 3 by hydrochloric acid, by water adjusted to a pH 3 to 4 and by non treated water and then the water layer is removed. The oil layer is thereafter dried by a vacuum pump (10–20mm Hg pressure) with heating to 120° C. to obtain PTMG. The obtained polymer is transferred to the 100 ml standard bottle and the color number (JIS K-1557, testing method for polyether for polyurethane) is measured.

Synthetic method of copolymer polyether polyol

To a 500ml flask was added 154.9 g of THF, 50 g of 3-methyl tetrahydofuran and 8.9 g of 70 wt. % $HClO_4$ aqueous solution. The solution was cooled to 5° C., titrated 48.0 g of acetic anhydride over 30 minutes, and then stirred for 8 hours at 5° C. After quenching the solution with 160.5 g of 17 wt. % aqueous solution of sodium hydroxide and stirring, the contents of the flask are allowed to settle and the water layer is removed. 50 g of 30 wt. % aqueous solution of sodium hydroxide is added to the oil layer, followed by heating to 120° C. to distill off the unreacted monomer, then 150 g of n-butanol are added and the solution is refluxed for 3 hours and saponificate the contents. After the contents are settled and the water layer is removed, 100 g of water is added to the oil layer. After heating the contents to reflux with constant stirring for 15 minutes, the contents of the flask are allowed to settle and cool, and, after the water layer is removed, the oil layer is rinsed by water. The oil layer is further rinsed 3 times by water adjusted to pH 2 to 3 by hydrochloric acid, by water adjusted to pH 3 to 4 and by non treated water and then the water layer is removed. After that, the oil layer is dried using a vacuum pump (10 to 20 mm Hg pressure) with heating to 120° C. and then PTMG can be obtained. The obtained polymer is transferred to the 100 ml standard bottle and the color number (JIS K-1557) is measured.

Comparative Example 1

200 g of crude THF (THF 99.16 PA %, dihydrofuran 0.15 PA %, others 0.69 PA %) is purified by rectification, and 194.6 g of THF (THF 99.50 PA %, dihydrofuran 0.12 PA %, others 0.38 PA %) is obtained. Using this purified THF as the starting material, PTMG is synthesized according to above mentioned method, and a PTMG of color number 140 is obtained in 70 wt. % yield.

Example 1

To 1000 g of crude THF used in Comparative Example 1, is added 1.0 g of concentrated sulfuric acid. The solution is allowed to stir for 1 hour at 50° C., at which time 2.0 g of 48 wt. % aqueous solution of sodium hydroxide is added to make the solution basic. After dehydration, a single distillation and rectification follow, and 925.0 g of purified THF (THF 99.50 PA %, dihydrofuran 0.12 PA %, others 0.38 PA %) is obtained. Using the obtained purified THF as the starting material, PTMG is synthesized according to above mentioned method, and PTMG of color number 10 is obtained in 70 wt. % yield.

Comparative Example 2

To the mixture composed of THF 67. 1%, water 9.9% and acetic acid 23.0%, high acid cationic ion exchanging resin is added, then reacted for 1 hour at 50° C. After the resin is filtered off, the reacted product is distilled and collected. The obtained liquid is held on a carrier of ruthenium activated carbon. The liquid is supplied to the reactor in which catalyst is packed together with 0.5 part/hour of hydrogen. This hydrogenation reaction is carried out at 100° C., 9.5 kg/cm² pressure and 0.5 hour residence time (vacant cylinder standard). Liquid collected from the reactor is purified and rectified to obtain purified THF (THF 99.50 PA %, dihydrofuran 0 PA %, others 0.30 PA %). Using the obtained purified THF as the starting material, PTMG is synthesized according to above mentioned Synthetic method of PTMC; and PTMG of color number 10 is obtained in 70 wt. % yield.

Comparative Example 3

200 g of crude 3-methyl THF (3-methyl THF 36.3 PA %, others 0.69 PA %) is purified by rectification, and 72.9 g of 3-methyl THF (3-methyl THF content 90 PA %, others 10.0 PA %) is obtained. Using the rectified 3-methyl THF and purified THF obtained by Example 1, THF/3-methyl THF copolymer is synthesized according to the mentioned Synthetic method of copolymer polyether polyol, and copolymer polyether polyol of color number 400 is obtained in 65 wt. % yield.

Example 2

To 200 g of crude 3-methyl THF which is used in Comparative Example 3, 10 g of conc. Sulfuric acid is added and stirred for 1 hour at 50° C. then cooled to 5° C., a further 18 g of 48 wt. % aqueous solution of sodium hydroxide is added to make the solution alkali. After dehydration, a single distillation and rectification follow, and 60 g of purified 3-methyl THF (3-methyl THF 94.4 PA %, others 5.6 PA %) is obtained. Using the rectified 3-methyl THF and purified THF obtained by Example 1, THF/3-methyl THF copolymer is synthesized according to the mentioned Synthetic method of copolymer polyether polyol, and a copolymer polyether polyol of color number 10 is obtained at 67.2 wt. % yield.

Example 3

To 200 g of crude 3-methyl THF which is used in Comparative Example 3, 10 g of concentrated sulfuric acid is added and stirred for 1 hour at 50° C. and the resin is filtered off, and then rectified. 70 g of purified 3-methyl THF (3-methyl THF content 94.1 PA %, others 5.9 PA %) is obtained. Using the rectified 3-methyl THF and purified THF obtained by Example 1, THF/3-methyl THF copolymer is synthesized according to the mentioned Synthetic method of copolymer polyether polyol, and a copolymer polyether polyol of color number 20 is obtained in 69.1 wt. % yield.
Effect of the Invention The purifying methods of tetrahydrofurans of this invention involve simplified processes that do not use expensive materials. The material responsible for causing coloring in the preparation of polyether polyol can be removed sufficiently regardless of the preparation method of crude THF. It is now possible to obtain polyether polyol without coloring by using purified tetrahydrofurans obtained from a method according to the present invention.

What is claimed is:

1. A method for purifying a crude tetrahydrofuran which is then suitable for the preparation of a polyether polyol comprising:

contacting said crude tetrahydrofuran represented by the general formula (1) with mineral acid selected from the group consisting of nitric acid, sulfuric acid and phosphoric acid, said contacting being conducted at a temperature from the room temperature up to the boiling point of said tetrahydrofuran, and then instantly distillating by at least one of a simple distillation or a rectification, wherein said general formula (1) is:

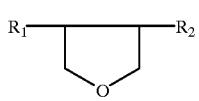
(1)

wherein $R_1$ and $R_2$ represent a hydrogen atom or an alkyl group of normal chain or graft whose carbon number is 1 to 5 and can be same or not be same.

2. The method for purifying a tetrahydrofuran according to claim 1, wherein said method comprises contacting said crude tetrahydrofurans with mineral acid, and then instantly distillating by at least one of a simple distillation or a rectification.

3. The method for purifying a tetrahydrofuran according to claim 1, wherein said method comprises contacting said crude tetrahydrofurans with mineral acid, to obtain an acidified solution, neutralizing the solution by adding an alkaline aqueous solution containing alkali metal or alkaline-earth metal in an amount which is more than an equivalent volume to the added volume of said mineral acid, and then instantly distillating by at least one of a simple distillation or a rectification.

4. The method for purifying a tetrahydrofuran according to anyone of claims 1, 2, and 3, wherein the volume of said mineral acid to be added is 0.1 to 15% by weight relative to the crude tetrahydrofurans.

5. The method for purifying a crude tetrahydrofuran which is then suitable for the preparation of a polyether polyol comprising contacting said crude tetrahydrofuran represented by the general formula (1):

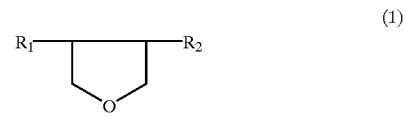
(1)

wherein $R_1$ and $R_2$ independently represent a hydrogen atom or a straight or branched alkyl group having 1–5 carbon atoms, with a high acid cationic ion exchange resin, wherein said high acid cationic ion exchange resin is a sulfonic acid type cationic ion exchange resin, and the quantity of said ion exchange resin to be added is 1 to 30% by weight relative to the crude tetrahydrofuran, and then conducting a least one of simple distillation or rectification and then recovering the purified tetrahydrofuran.

6. The method for purifying a tetrahydrofuran according to claim 1 or 2, wherein contacting the crude tetrahydrofuran with said mineral acid and the purifying of the crude tetrahydrofuran by said mineral acid and the distilling as a single distillation are carried out at the same time.

7. The method for purifying a tetrahydrofuran according to claim 3, wherein said alkaline aqueous solution is an aqueous sodium hydroxide or potassium hydroxide solution.

8. The method for purifying a tetrahydrofuran according to claim 1, wherein said method for purifying tetrahydrofurans is carried out in series.

9. The method for purifying a tetrahydrofuran according to claim 1, 2 or 5, wherein said tetrahydrofuran represented by said general formula (1) is 3-alkyl tetrahydrofuran.

10. The method for purifying a tetrahydrofuran according to claim 9, wherein said tetrahydrofuran represented by said general formula (1) is 3-methyl tetrahydrofuran.

11. The method for purifying a tetrahydrofuran according to claim 9, wherein said tetrahydrofuran represented by said general formula (1) is 3-ethyl tetrahydrofuran.

* * * * *